United States Patent [19]

Palson et al.

[11] 4,301,949

[45] Nov. 24, 1981

[54] DEODORANT DISPENSING DEVICE

[75] Inventors: Richard C. Palson, Medfield; John C. Armstrong, Milton, both of Mass.

[73] Assignee: The Pharmasol Corporation, Randolph, Mass.

[21] Appl. No.: 73,233

[22] Filed: Sep. 7, 1979

[51] Int. Cl.³ .............................................. A61L 9/04
[52] U.S. Cl. ................................. 222/548; 222/565; 239/56; 239/59
[58] Field of Search .............. 222/548, 557, 555, 565; 239/59, 58, 56, 55, 57; 285/162; 220/231; 215/310

[56] References Cited

U.S. PATENT DOCUMENTS

| | | | |
|---|---|---|---|
| 1,732,028 | 10/1929 | Reiner | 239/59 X |
| 2,086,631 | 7/1937 | Munro | 239/59 X |
| 2,657,090 | 10/1953 | Meek | 239/59 X |
| 2,777,616 | 1/1957 | DeShazor | 222/555 |
| 2,817,451 | 12/1957 | Giles et al. | 222/548 X |
| 3,081,011 | 3/1963 | Stull | 222/548 X |
| 3,140,804 | 7/1964 | Frank | 222/548 X |
| 3,844,588 | 10/1974 | Jocsak | 285/162 |
| 4,096,994 | 6/1978 | Bryson | 239/57 |
| 4,120,432 | 10/1978 | Fuchs | 222/565 |

FOREIGN PATENT DOCUMENTS

| | | | |
|---|---|---|---|
| 1056510 | 10/1953 | France | 239/57 |
| 560143 | 3/1975 | Switzerland | 239/59 |

Primary Examiner—Robert J. Spar
Assistant Examiner—Frederick R. Handren
Attorney, Agent, or Firm—Robert E. Meyer

[57] ABSTRACT

A deodorant dispenser of the kind comprising a receptacle containing a pad impregnated with a deodorant material wherein the receptacle is provided with relatively rotatable top parts containing openings which on the one hand may be aligned by rotation of the parts and on the other hand positioned to be partially or completely out of alignment.

9 Claims, 10 Drawing Figures 4,301,949

DEODORANT DISPENSING DEVICE

BACKGROUND OF THE INVENTION

The provision of relatively rotatable parts at the top of a dispensing receptable to permit on the one hand dispensing a material from the receptacle and on the other hand to prevent loss of material from the receptacle to old in the art. Such devices usually comprise a flat, perforated part at the top of the receptacle and a superimposed closure rotatably fastened to the top part by, for example, rivets or other fastneing means. The dispensing device of this invention is generally similar in makeup in that it has a perforated top and a superimposed closure rotatably applied thereto, but, in contrast, the container top and closure are especially designed to enable manufacturing the receptacle and closure of plastic materials by conventional molding operations and assembly thereof without fastening elements.

SUMMARY OF THE INVENTION

As herein illustrated, the deodorant dispensing device comprises in combination a receptacle for receiving a pad saturated with deodorant material, means at the top of the receptacle defining a plurality of openings disposed circularly about a common center, a closure positioned at the top and containing a plurality of correspondingly-located openings and mutually interengageable means at the interfaces of the top and closure rotatably retaining the closure in engagement with the top. More specifically, the top contains a circular depression having a flat bottom and the openings are formed at the bottom of the depression. The closure is a disk disposed in said circular depression for rotation therein so that rotation of the disk within the depression on the one hand positions the openings in total alignment and on the other hand partially or completely out of alignment. The disk corresponds substantially in thickness to the depth of the depression so that the top of the closure is substantially flush with the surface of the top bounding the depression. The mutually interengageable means comprise a circular groove peripherally of the bottom of the recess and a circular rib at the bottom side of the closure which mates with and is rotatably engaged within said recess. Additionally, there is mutually interengageable means at the center of the bottom of the depression and at the center of the bottom side of the closure which rotatably support the closure in concentric relation with the depression comprising means at the center of the bottom of the depression defining a circular bearing surface concentric with the center of depression and means at the bottom side of the closure defining a mating bearing surface. The bearing surfaces are hemispherical. There is an opening at the center of the bearing surface at the bottom of the depression and means at the center of the bearing surface at the bottom side of the closure arranged to extend through the opening to releasably hold the closure within the depression. The latter means comprises flexibly yieldable fingers, the lower ends of which are provided with inwardly inclined surfaces designed to facilitate thrusting the fingers through the opening and outwardly-disposed surfaces designed by engagement with the edge of the opening to retain the bearing surfaces interengaged.

The invention will now be described in greater detail with reference to the accompanying drawings, wherein.

Figure 1:
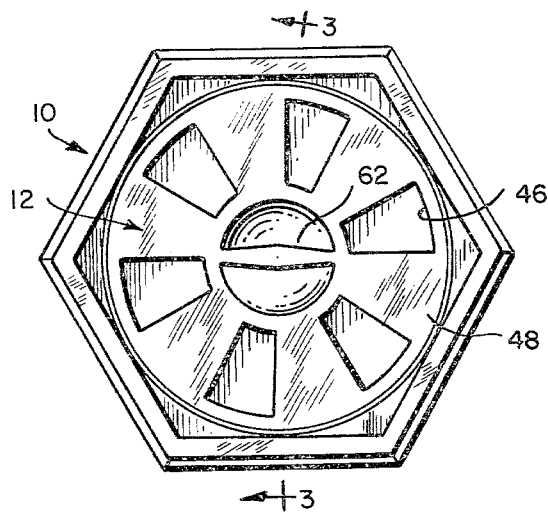
FIG. 1 is a plan view of the deodorant dispenser.
Figure 2:
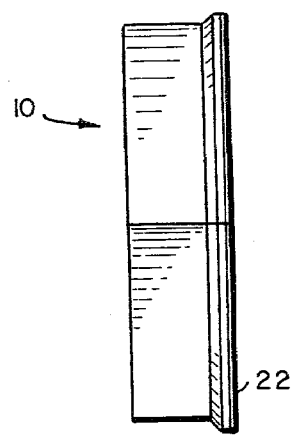
FIG. 2 is an elevation viewed from the right side of FIG. 1.
Figure 3:
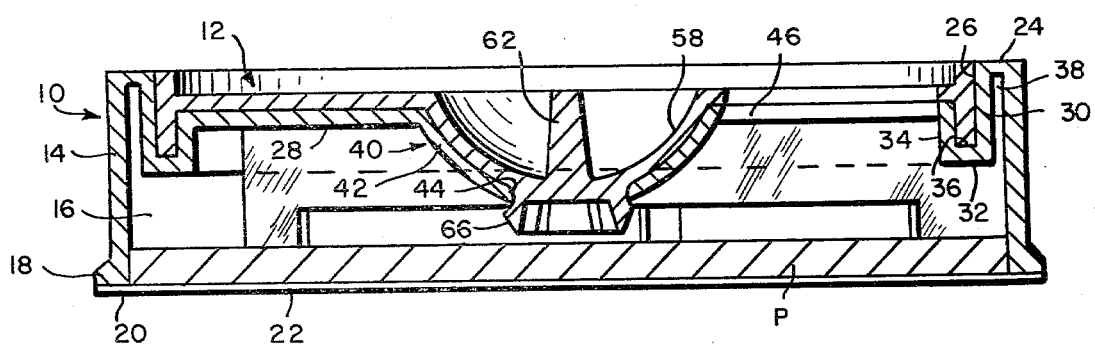
FIG. 3 is an enlarged section taken in the line 3—3 of FIG. 1.
Figure 4:
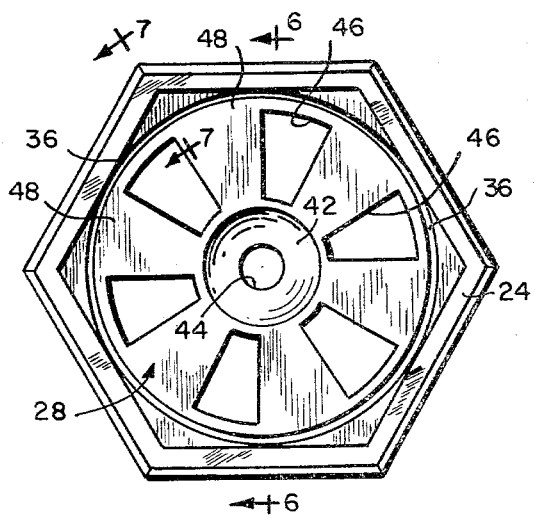
FIG. 4 is a top plan view of the component part of the dispenser comprising the receptacle.
Figure 5:
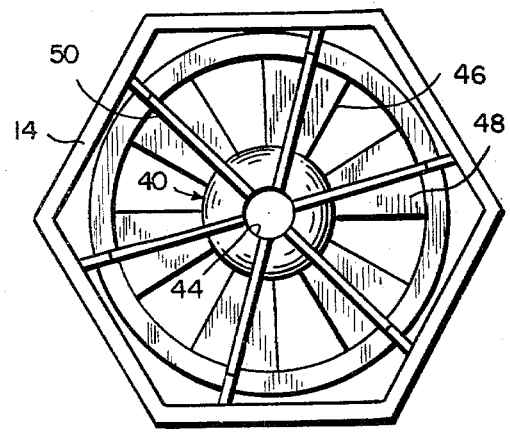
FIG. 5 is a bottom view of FIG. 4.
Figure 6:
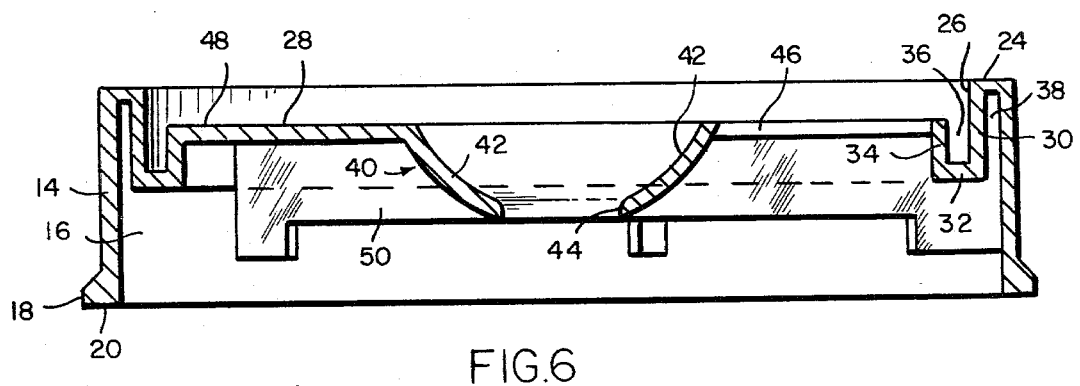
FIG. 6 is an enlarged section taken on the line 6—6 of FIG. 4.
Figure 7:
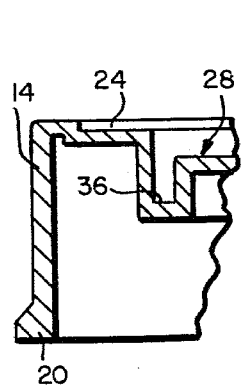
FIG. 7 is a fragmentary plan view taken on the line 7—7 of FIG. 4.
Figure 8:
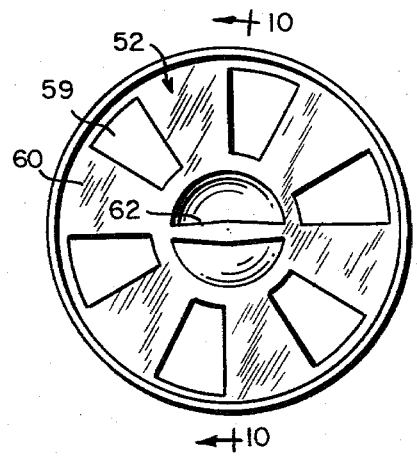
FIG. 8 is a top plan view of the component part of the dispenser comprising the cap.
Figure 9:
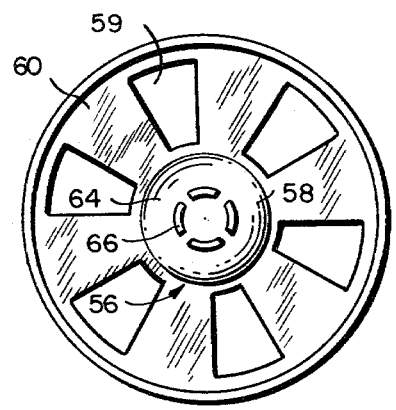
FIG. 9 is a bottom view of FIG. 8.

Referring to the drawings, FIGS. 1, 2 and 3, the dispenser receptacle as herein illustrated is designed to receive a pad impregnated with a deodorant material and comprises in general a receptacle 10 provided at its top with a rotatable closure 12 designed by rotation to at times close the receptacle so as to prevent escape of the deodorant and at other times to open the top varying degrees to permit dispensing the doedorant.

The receptacle 10 as shown in FIG. 3 is of polygonal section and comprises side walls 14 which define an interior chamber 16 bounded at one end by a peripheral, radially-extending flange 18 which provided, in conjunction with the end, a relatively broad, flat planar surface 20 to which a sheet material 22 may be cemented or otherwise fastened to form a bottom for the receptacle. The sheet material 22 may be, for example, cardboard, foil or plastic. At the other ends of the side walls 14 which is the upper end of the receptacle with respect to the bottom, there is an inwardly-extending planar portion 24 which constitutes the top of the receptacle and defines a circular opening 26 concentric with the center. Within the circular opening 26 there is a depressed part 28 supported in spaced, parallel relation to the planar portion 24 by a peripheral, downwardly-extending wall portion 30 a peripherally-extending, horizontal wall portion 32 and an upwardly-extending wall portion 24. The upper end of the wall portion 30 is integral with the planar portion 24 and the upper end of the wall portion 34 is integral with the part 28. The wall portion 30 is spaced from and parallel to the wall portion 34 and defines, in conjunction with the wall portion 32, an annular groove 36 peripherally of the part 28. The wall portion 30 is parallel to the side wall 14 and defines therewith an annular space 38.

At the center of the depressed part 28, there is a centrally-located, downwardly-extending bearing component 40 having an inner hemispherical surface 42 and at its bottom a circular opening 44. Peripherally of the bearing component 40 there are radially-disposed, peripherally-spaced openings 46 of generally truncated, triangular configuration with their bases adjacent the groove 36 and their truncated apices adjacent the bearing component 40. There are imperforate portions 48 between the openings 46, correspondingly generally truncated triangles with their bases located adjacent the groove and their truncated apices adjacent the bearing component. The openings 46 and the imperforate portions 48 therebetween are of substantially the same circular dimension.

At the undersides of the imperforate portions 48, there are vertically-disposed stiffening ribs 50 connected at one end to the outer peripheral surface of the bearing component 40 and at their other ends to the inner side of the side walls 14. The upper edges of these reinforcing ribs 50 are connected to the imperforate portions 48, to the inner sides of the wall portions 50 and to the lower sides of the wall portions 32.

Figure 10:
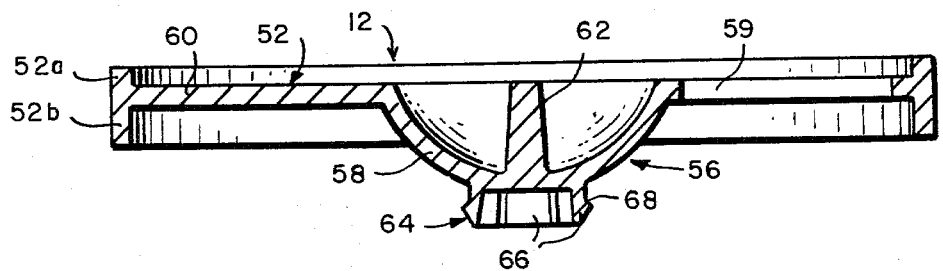
FIG. 10 is an enlarged section taken on the line 10—10 of FIG. 8.

The closure 12, FIG. 10, which as heretofore explained is rotatable with respect to the top of the receptacle comprises a flat, circular disk 52 provided with a peripheral, upwardly-extending flange 52a and is of a diameter corresponding substantially to the inside diameter of the opening 26 at the top of the receptacle. At the lowr side of the disk 52, there is a peripheral, downwardly-extending circular flange 52b dimensioned to fit into the groove 36 for supporting the disk for rotation relative to the part 28. The disk is further supported for rotation with respect to the part 28 by a downwardly-extending bearing component 56 at its center, the outer surface 58 of which is spherically convex and designed to nest snugly within the concave surface 42 of the bearing component 40.

The closure disk 52 contains peripherally of the bearing component 56 radially-disposed, peripherally-spaced openings 59 interspersed with imperforate portions 60. The openings 58 and imperforate portions 60 correspond substantially in spacing and dimension to the openings and intermediate portions 46 ad 48, respectively, of the part 28 so that, by rotation of the disk 52, the openings 59 may be disposed in total alignment with the openings 46 so as to permit maximum dispensing or partially or totally closed to control the rate of dispensing or to prevent dispensing entirely.

Desirably, the upper surface of the bearing component 56 is downwardly concave and a diametrically-disposed nub 62 is fixed therein which provides a convenient means for rotating the disk 54 relative to the part 28.

In order to rotatably hold the closure disk 52 engaged with the part 28, there is provided snap-on means 64 which is designed to enable easily assembling the disk to the top of the receptacle for maintaining the disk in rotatable engagement therewith and to removably hold the disk to the part 28. This is achieved by means of a plurality of peripherally-disposed, downwardly-extending, flexibly-resilient finers 66 spaced about the lower end of the bearing component 56 which are elastically engaged within the opening 44 in the bearing component 40. The fingers 66 are provided with inwardly-inclined surfaces 67 which facilitate thrusting them through the opening 44 and outwardly-disposed surfaces 68 which, by engagement with the lower edge of the opening 44 after the fingers are thrust through the opening, lock the disk in place while permitting it to rotate freely in the depression and also removable by the application of pressure from inside if it is found desirable to do so.

The device as thus described is completely molded of plastic and, after the parts have been completed, an absorbent pad P such as described above impregnated with a deodorant, for example, a liquid deodorant, is placed within the lower end of the receptacle and the bottom sheet 22 adhesively attached to the widened lower edge. Thereafter, the closure cap 12 is placed in the recess and pressed downwardly to engage the fingers 66 within the hole 44. It is to be noted that the top of the flange 52a is substantially flush with the top surface 24 of the receptacle.

As herein illustrated, the receptacle is hexagonal; however, it is within the scope of the invention to provide it with a different number of sides or to make it circular or oval in configuration. Additionally, the number of the openings in top of the receptacle and closure may be increased or decreased and their configuration modified without departing from the spirit and scope of the invention.

It should be understood that the present disclosure is for the purpose of illustration only and inlcudes all modifications or improvements which fall within the scope of the appended claims.

What is claimed is:

1. A deodorant dispensing device comprising in combination a receptacle for receiving a pad saturated with deodorant material, means at the top of the receptacle defining a plurality of openings disposed about a common center, a closure positioned at the top of the receptacle in mating engagement therewith and containing a plurality of corresponding located openings, mutually interengageable snap-on means at the interfaces of the closure and top for assembly of the closure to the top and rotatably retaining the closure in operative position, said mutually interengageable means including a downwardly extending bearing component in both said top and said closure, said downwardly extending bearing component comprising a hemispherical bearing surface concentric with the center of said top and a mating hemispherical bearing surface on the underside of said closure concentric with the center thereof, and means including a diametrically disposed nub in said bearing component for said closure for rotating said closure relative to said top.

2. A deodorant dispensing device according to claim 1 wherein the mutually interengageable means are elastically interengaged.

3. A deodorant dispensing device according to claim 2 wherein the means at the top of the receptacle includes a circular depression within which said openings are circularly arranged and uniformly spaced at the bottom thereof, wherein said closure includes rotatable means disposed in said circular depression for rotation therein, the said openings in said closure being circularly arranged, and uniformly spaced to correspond to those in said depression, the spacing of the openings being such that the rotatable means may be rotated within the depression to on the one hand position the openings in total alignment and on the other hand position them partially or completely out of alignment, said depression having at its bottom a circular groove peripherally thereof and said rotatable means having at its bottom side a circular rib which mates with and is rotatably engaged within said groove.

4. A deodorant dispensing device according to claim 3 wherein said closure is a flat disk corresponding substantially in diameter to the diameter of the circular depression.

5. A deodorant dispensing device according to claim 4 wherein the openings at the bottom of the depression and the openings in the disk are radially-disposed with respect to the center of rotation of the disk.

6. A deodorant dispensing device according to claim 1 wherein the bearing surface at the center of said top is provided with a center opening and the bottom of the bearing surface at the center of said closure is provided with engaging means adapted to be rotatably engaged with said opening for retaining said closure on said top.

7. A deodorant dispensing device according to claim 6 wherein said engaging means comprise flexibly yieldable fingers adapted to engage within the hole frictionally resisting disengagement of the bearing surfaces and, hence, of the closure from the top.

8. A deodorant dispensing device according to claim 7 wherein said fingers have at their lower ends inwardly-inclined surfaces designed to facilitate thrusting the fingers through the opening.

9. A deodorant dispensing device according to claim 8 wherein said fingers have outwardly disposed surfaces designed by engagement with the edge of the opening to lock the bearing surfaces together.

* * * * *